(12) United States Patent
Schneider et al.

(10) Patent No.: US 7,211,180 B2
(45) Date of Patent: May 1, 2007

(54) CONTAMINATION-RESISTANT GAS SENSOR ELEMENT

(75) Inventors: Jens Stefan Schneider, Anderson, SC (US); James Richard Waldrop, Belton, SC (US); Velma Viane Massey, Williamston, SC (US); Donald Stanley Frost, Jr., Belton, SC (US)

(73) Assignee: Robert Bosch Corporation, Broadview, IL (US)

( * ) Notice: Subject to any disclaimer, the term of this patent is extended or adjusted under 35 U.S.C. 154(b) by 455 days.

(21) Appl. No.: 10/361,872

(22) Filed: Feb. 10, 2003

(65) Prior Publication Data

US 2004/0154920 A1    Aug. 12, 2004

(51) Int. Cl.
  *G01N 27/407* (2006.01)
(52) U.S. Cl. .................... 204/429; 427/99.2
(58) Field of Classification Search ........... 204/424, 204/429; 427/58, 99.2
  See application file for complete search history.

(56) References Cited

U.S. PATENT DOCUMENTS

| 4,257,863 | A |   | 3/1981  | Hoffman          |         |
|-----------|---|---|---------|------------------|---------|
| 4,272,349 | A |   | 6/1981  | Furutani et al.  |         |
| 4,279,666 | A |   | 7/1981  | Micheli          |         |
| 4,296,148 | A |   | 10/1981 | Friese           |         |
| 4,331,632 | A | * | 5/1982  | Galloway         | 422/206 |
| 4,356,065 | A |   | 10/1982 | Dietz            |         |
| 4,402,821 | A |   | 9/1983  | Yan              |         |
| 4,409,127 | A |   | 10/1983 | Keppel et al.    |         |
| 4,500,412 | A |   | 2/1985  | Takahashi et al. |         |
| 4,502,939 | A |   | 3/1985  | Holfelder et al. |         |
| 4,584,086 | A |   | 4/1986  | Hayakawa et al.  |         |
| 4,655,892 | A |   | 4/1987  | Satta et al.     |         |
| 4,828,807 | A | * | 5/1989  | Domesle et al.   | 423/213.7 |
| 4,851,105 | A |   | 7/1989  | Ishiguro et al.  |         |
| 4,859,307 | A |   | 8/1989  | Nishizawa et al. |         |
| 4,863,583 | A |   | 9/1989  | Kurachi et al.   |         |
| 4,985,126 | A | * | 1/1991  | Haefele et al.   | 205/779.5 |
| 5,006,221 | A |   | 4/1991  | Uchikawa et al.  |         |
| 5,160,598 | A |   | 11/1992 | Sawada et al.    |         |
| 5,169,513 | A |   | 12/1992 | Mase et al.      |         |
| 5,174,885 | A |   | 12/1992 | Hayakawa et al.  |         |
| 5,268,086 | A |   | 12/1993 | Hamburg et al.   |         |
| 5,271,816 | A |   | 12/1993 | Tanaka et al.    |         |
| 5,271,821 | A |   | 12/1993 | Ogasawara et al. |         |
| 5,302,276 | A |   | 4/1994  | Kato et al.      |         |
| 5,310,575 | A |   | 5/1994  | Friese et al.    |         |

(Continued)

FOREIGN PATENT DOCUMENTS

EP    1 154 263    11/2001

(Continued)

*Primary Examiner*—Kaj K. Olsen
(74) *Attorney, Agent, or Firm*—Michael Best & Friedrich LLP

(57) ABSTRACT

A contamination-resistant sensor element and methods for making the same are provided. A sensor element may include a contamination-resistant coating on at least a portion thereof. The coating may comprise gamma-delta alumina and lithium oxide and may have a thickness of about 100 to about 600 microns and a porosity of about 20 to about 70 percent. The method may include using gamma-delta alumina and lithium oxide to form a mixture, applying the mixture to at least a portion of a sensor element, and temperature treated the mixture to form a contamination-resistant coating on the surface of the measuring cell.

32 Claims, 5 Drawing Sheets

U.S. PATENT DOCUMENTS

| | | | |
|---|---|---|---|
| 5,368,713 A | 11/1994 | Friese et al. | |
| 5,380,424 A | 1/1995 | Friese et al. | |
| 5,419,828 A | 5/1995 | Nakano et al. | |
| 5,435,901 A | 7/1995 | Friese et al. | |
| 5,443,711 A | 8/1995 | Kojima et al. | |
| 5,486,279 A | 1/1996 | Friese et al. | |
| 5,492,612 A | 2/1996 | Kennard, III et al. | |
| 5,593,558 A | 1/1997 | Sugino et al. | |
| 5,685,964 A | 11/1997 | Watanabe et al. | |
| 5,766,434 A | 6/1998 | Fujii et al. | |
| 5,773,894 A | 6/1998 | Friese et al. | |
| 5,814,285 A | 9/1998 | Kojima et al. | |
| 5,849,165 A | 12/1998 | Kojima et al. | |
| 5,925,814 A * | 7/1999 | Tsuzuki et al. | 73/23.32 |
| 5,948,225 A | 9/1999 | Katafuchi et al. | |
| 5,997,707 A | 12/1999 | Kato et al. | |
| 6,007,688 A | 12/1999 | Kojima et al. | |
| 6,184,416 B1 | 2/2001 | Ding et al. | |
| 6,203,678 B1 | 3/2001 | Leonhard et al. | |
| 6,350,357 B1 | 2/2002 | Wiedenmann et al. | |
| 6,409,899 B1 | 6/2002 | Satou et al. | |
| 6,777,370 B2 * | 8/2004 | Chen | 502/241 |
| 2002/0102347 A1 | 8/2002 | Clyde et al. | |
| 2002/0103078 A1 | 8/2002 | Hu et al. | |

FOREIGN PATENT DOCUMENTS

| | | |
|---|---|---|
| EP | 1 164 371 | 12/2001 |
| EP | 1 195 601 | 4/2002 |
| EP | 1 125 488 | 6/2002 |
| WO | WO 89/04480 | 5/1989 |

* cited by examiner

US 7,211,180 B2

CONTAMINATION-RESISTANT GAS SENSOR ELEMENT

BACKGROUND OF THE INVENTION

A wide variety of gas sensors and gas sensor elements are used to measure different gases. More particularly, a sensor element of an exhaust gas sensor may be used in automotive applications to measure different gases (e.g., oxygen) in the exhaust gas.

Over time, however, different components in the exhaust gases tend to contaminate different parts of the gas sensor. More specifically, components such as lead, phosphorus, silicon, manganese, zinc, calcium, phosphates, oil ashes, rusts, metal oxides and other elements in the exhaust gas may tend to contaminate the electrode. More particularly, an outer electrode of the sensing element may be contaminated, and the porosity of the protective layer system may also be clogged, eventually affecting the functioning of the sensor and sometimes rendering the sensor or sensor element inoperable. Acidic exhaust components such as $P_xO_y$ and $SO_x$, wherein x and y are positive whole numbers, may also contaminate the sensor element, as well as reactive catalyst poisons such as lead, silicon and bismuth compounds. As a result, protective coatings are continually being sought in order to inhibit and/or prevent contamination of sensor elements and gas sensors.

SUMMARY OF THE INVENTION

In one aspect, the invention may provide a sensor element comprising a contamination-resistant coating on at least a portion thereof. The coating may comprise gamma-delta alumina and lithium oxide. The coating may or may not further comprise at least one of titanium oxide, lanthanum oxide, boehmite alumina and a combination thereof.

In another aspect, the invention may provide a method of making a contamination-resistant sensor element. The method generally includes using gamma-delta alumina and a lithium compound to form a mixture, applying the mixture to at least a portion of a sensor element, and temperature treating the mixture to form a contamination-resistant coating on the sensor element. The other oxides listed above may or may not be used to form the mixture.

DETAILED DESCRIPTION OF THE INVENTION

Figure 1:
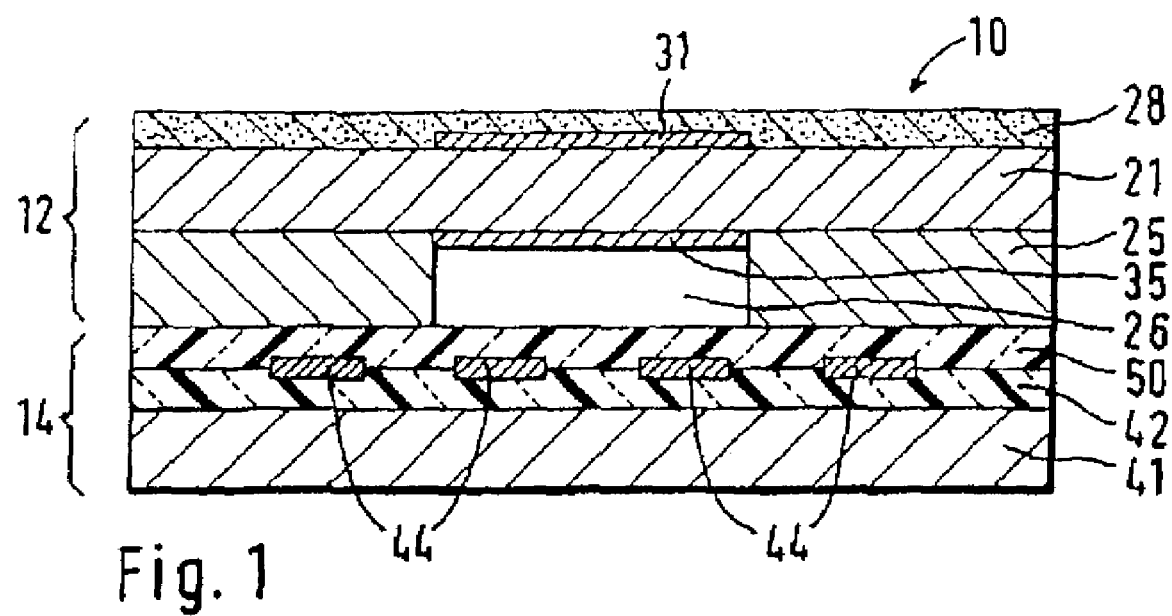
FIG. 1 shows a cross-section through an exhaust-gas-side part of a sensor element.
Figure 2:
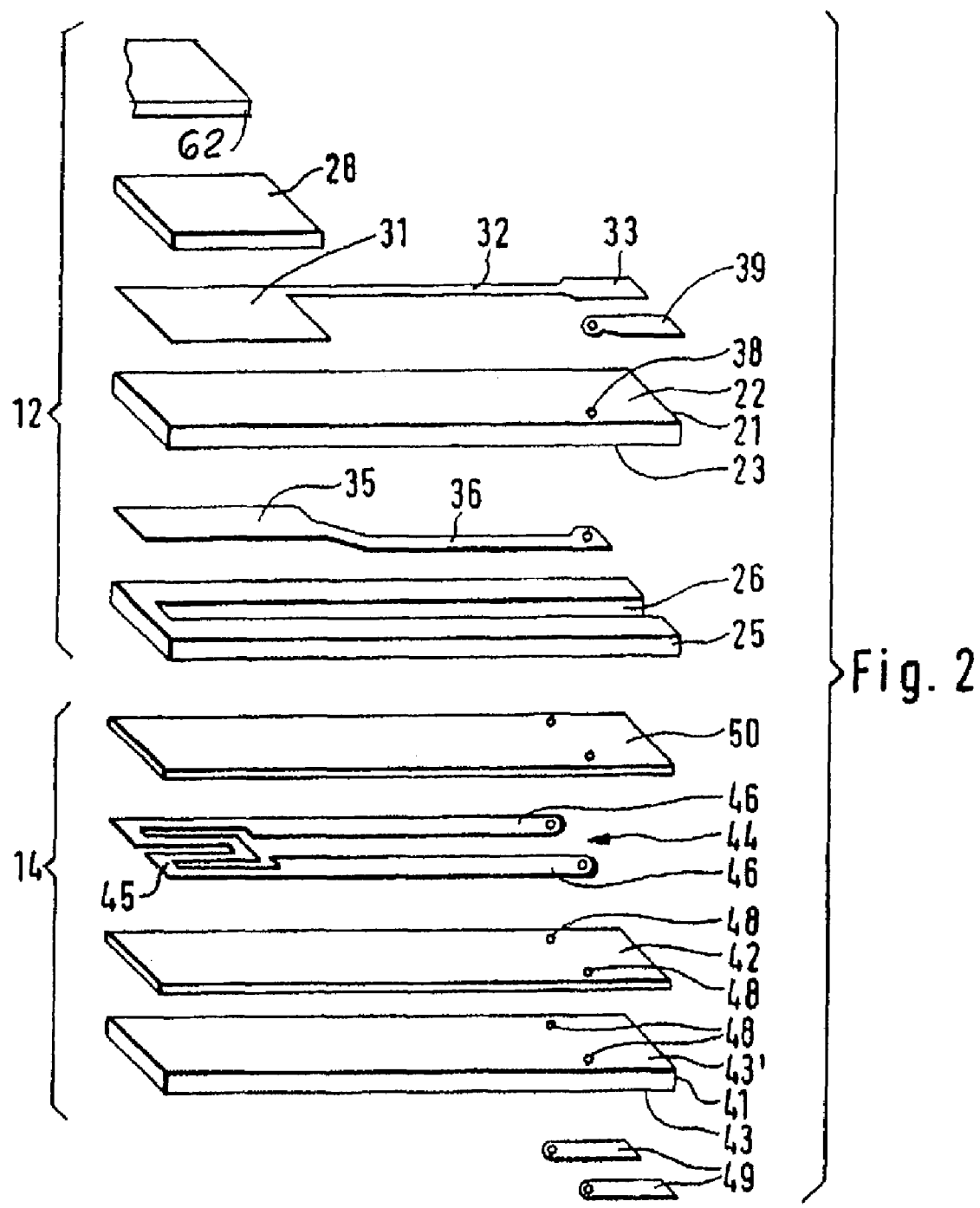
FIG. 2 shows an enlarged view of a layer system of the sensor element illustrated in FIG. 1.

A plate-shaped or planar sensor element 10 of an automotive gas sensor element is illustrated in the figures as described above. The protective coatings described herein may be applied to this specific sensor planar sensor element (described below), as well as to a wide variety of sensor elements as will be understood by those of ordinary skill in the art. In other words, the application of the protective coatings of the present invention as described herein should in no way be limited to the particular sensor element described below. Sensor element 10 is intended to be one illustrative example.

The sensor element 10 of the figures has an electrochemical measuring cell 12 and a heating element 14. Measuring cell 12 has, for example, a first solid electrolyte foil 21 with a top surface 22 on the measured gas side and a large surface 23 on the reference gas side, as well as a second solid electrolyte foil 25 with a reference channel 26 integrated therein. On large surface 22 on the measured gas side there is a measuring electrode 31 with a printed conductor 32 and a first terminal contact 33. On large surface 23 on the reference gas side of first solid electrolyte foil 21, there is a reference electrode 35 with a printed conductor 36. Furthermore, a through-plating 38 is provided in first solid electrolyte foil 21, through which printed conductor 36 of reference electrode 35 is guided to large surface 22 on the measured gas side. In addition, first terminal contact 33, a second terminal contact 39, connected to through-plating 38 and thus forming the contact point for reference electrode 35, is also located on large surface 22. Measuring electrode 31 is covered with a porous protective layer 28.

The porous protective layer 28 may comprise at least one of a zirconium oxide, aluminum oxide, titanium oxide, magnesium oxide, and a combination thereof. The porosity of the coating is generally greater than about 10 percent, and more particularly, greater than about 25 percent. The porosity is usually less than about 75 percent, and more particularly, less than about 55 percent. Generally the protective layer 28 is sintered at a high temperature and is mechanically very robust but its capacity to absorb contaminants is considerably lower than that of protective layer 62. The thickness of the layer 28 may be greater than about 30 microns. Generally, the thickness of the layer 28 is less than about 250 microns.

The heating element 14 has, for example, a support foil 41 with an outer large surface 43 and an inner large surface 43', which, in this embodiment is composed of the material of the two solid electrolyte foils 21, 25. An outer insulation layer 42 may be applied to inner large surface 43' of support foil 41. A resistance heater 44 with a wave-form heating conductor 45 and two terminal conductors 46 is located on outer insulation layer 42. Outer insulation layer 42 and support foil 41 have two heater through-platings 48 each flush to one another, which run from the two terminal conductors 46 to outer large surface 43 of support foil 41. Two heater terminal contacts 49 are arranged on outer large surface 43 of support foil 41, which are connected to heater through-platings 48.

An inner insulation layer 50 is on resistance heater 44. The large surface of inner insulation layer 50 is connected to the large surface of the second solid electrolyte foil 25. Thus heating element 14 is thermally connected to measuring cell 12 via inner insulation layer 50.

The two solid electrolyte foils 21 and 25 and support foil 41 may be composed of $ZrO_2$, partially stabilized with 5 mol. percent $Y_2O_3$, for example. Electrodes 31, 35, printed conductors 32, 36, through-platings 38 and terminal contacts 33, 39 are made of platinum cermet, for example. In this embodiment, a platinum cermet is also used as the material for the resistance heater, the ohmic resistance of leads 46 being selected to be less than that of heating conductor 45.

Two of the properties of a contamination protective layer may be the following: a) high mechanical and hydrothermal stability, even when applied as a thick layer; and b) high absorbency for contaminants, i.e., chemical reactivity. However, these two properties may in part, conflict with each other. Generally, the more reactive a material, the less durable and robust it is. The compositions, application methods, and design features described herein may allow for the manufacturing of a protective layer with superior protective power while maintaining sufficient mechanical and hydrothermal robustness for long term use.

A mixture that can be fired to form a contaminated-resistant coating may be applied directly or indirectly (discussed in more detail below) to the measuring electrode 31. The coatings are particularly adept at inhibiting, preventing or resisting contamination on the surface to which it is applied by one or more, or a combination thereof, of the contaminants discussed in the Background. As used herein, the term "mixture" is meant to refer to a mixture of one or more ingredients before being temperature treated. The "coating" 62 is the product of temperature treating the mixture.

Generally, the mixture comprises at least one of a form of alumina and a form of lithium oxide. More particularly, the alumina may be at least one of gamma-delta alumina, boehmite alumina, alpha alumina, beta aluminates and combinations thereof. Suitable boehmite alumina may be obtained from Reade Corporation located in Providence, R.I. or Sasol, Inc. located in Houston, Tex. Suitable alpha alumina can be obtained from Sumitomo located in New York, N.Y. Suitable lithium components, which convert into oxides after temperature treatment, can be obtained from Sigma-Aldrich Corporation located in Milwaukee, Wis.

Generally, the mixture may comprise at least about 20 percent by weight gamma-delta alumina, more particularly greater than about 22 percent by weight, and even more particularly, greater than about 25 percent. Generally, less than about 40 percent by weight of the mixture will be gamma-delta alumina. More particularly, the mixture may comprise less than about 35 percent by weight, and even more particularly, less than about 30 percent by weight gamma-delta alumina. The surface area (measured in $m^2/g$) of the gamma-delta alumina will generally be greater than about 90, and more particularly, greater than about 130. The surface area of the gamma-delta alumina (when used) will generally be less than about 230, and more particularly, less than about 170.

The mixture may or may not also comprise boehmite alumina to replace the gamma delta alumina in part. When used, the mixture may comprise at least about 1 percent by weight boehmite alumina, and more particularly, greater than about 5 percent or about 8 percent. The mixture will usually comprise less than about 20 percent, and more particularly, less than about 18 percent or less than about 15 percent by weight. The surface area (measured in $m^2/g$) of the boehmite alumina (when used) will generally be greater than about 100, and more particularly greater than about 120. The surface area of the boehmite alumina will generally be less than about 190, and particularly less than about 160.

Other types of alumina that may be used in the mixture include, but are not limited to, alpha alumina and beta aluminates to replace gamma delta alumina in part. These aluminas and aluminates, when used, may comprise greater than about 1 percent by weight of the mixture. Generally, less than about 10 percent by weight of the aluminas are used. The surface area of the alumina is generally greater than 2 $m^2/g$. The surface area may also be less than about 85 $m^2/g$.

Generally, the mixture may comprise at least about 0.5 weight percent lithium oxide, more particularly more than about 2 percent, and even more particularly more than about 4 percent. Other lithium compounds that convert to lithium oxide after temperature treatment may also be used in similar amounts.

The mixture may also comprise one or more low-temperature binders. As used herein, a "low-temperature binder" is meant to refer to an organic compound soluble or dispersed in water or solvents. The low-temperature binder functions to bind the oxide particles during and after application and before heat-treating. Examples of low-temperature binders include, but are not limited to, polyacryl resins, hydroxyethylcellulose (HEC), other cellulose derivatives, polyvinyl alcohol (PVA), polyvinyl pyrrolidone (PVP) polyvinyl acetates (PVAc), polyacrylic resins, and combination thereof. Generally, at least about 0.5 percent by weight of low-temperature binder may be used. Greater than about 2 percent by weight, and even more particularly about 4 percent by weight low-temperature binder may also be used. Generally, less than about 10 percent by weight low-temperature binder may be used, although less than about 8 percent by weight, and even less than about 6 percent by weight can be used.

The mixture may or may not also comprise one or more high-temperature binders. As used herein, "high-temperature binder" is meant to refer to a soluble or dispersed inorganic compound which provide adhesive strength between particles and between particles and substrate surfaces after temperature treatment. Examples of high-temperature binders include, but are not limited to, hydroxides of B, Al, and nitrates or acetates of Al, Mg and La. Generally, at least about 0.01 percent by weight of high-temperature binder may be used. More particularly, greater than about 0.5 percent by weight, and even greater than about 1 percent by weight of high-temperature binder may be used. Generally, less than about 8 percent by weight high-temperature binder may be used, although less than about 6 percent by weight, and even less than about 5 percent can be used.

The mixture may be water-based or solvent-based. Examples of suitable solvents include, but are not limited to, ethanol or isopropanol. When water is used as the base material for the mixture, the mixture will generally comprise at least about 45 percent by weight water, more particularly, at least about 50 percent, and usually at least about 55 percent by weight. Less than about 85 percent by weight of water may be used including less than about 70 by weight, and even less than about 60 by weight. When solvents or solvent water mixtures are used, similar weight ratios apply.

The mixtures may also include at least one of glass powder, lanthanum oxide, reactive Group IIA-oxides, magnesium titanate, lithium salts, zinc oxide, and combinations thereof. These compounds may be used in order to ensure mechanical stability, porosity and absorbent capacity. Specific examples of lithium salts include, but are not limited to, lithium chloride, lithium nitrate, lithium carbonate, lithium acetate, lithium citrates, and combinations thereof. These compounds are generally present in amounts greater than 0.5 percent by weight of the mixture. Less than about 5.0 weight percent by weight of the mixture is generally used.

These components are generally mixed with a stirrer or similar device. The low temperature binder is generally first added to the water or solvent and mixed for several minutes. The alumina is then added and allowed to mix for about 15 to about 25 minutes, and usually about 20 minutes. The gamma-delta alumina and lithium compound are then added slowly, e.g., about 2 grams per minute, while stirring. Finally, the high temperature binder and other components may be then added. The mixture is stirred for about 20 to about 40 minutes, and generally about 30 minutes before use.

During the mixing process, the low temperature binder is first added to the water or solvent and mixed for several minutes with a stirrer. The mixture is then transferred to a dissolver pot. The remaining solids, boehmite alumina, gamma delta alumina, and high temperature binder are then added to the pot. The dissolver pot is then loaded into the dissolver and sealed shut. The dissolver is then started. The dissolver is run at 1000 RPM's with cooling water ON for 10 minutes. The mixture is then discharged from the dissolver pot into a beaker and put under a stirrer at low speed for continuous agitation until it is needed.

The mixtures tend to possess certain physical and chemical properties. For example, depending upon the types and amounts of organic binder and ceramic filler being used, the mixture is likely to have a viscosity of at least about 50 mPas, more particularly greater than about 200 mPas, and even more particularly at least about 1000 mPas. The viscosity is also likely to be less than about 12,000 mPas, more particularly less than about 6500 mPas, and even more particularly less than about 3000 mPas. Depending on its viscosity, the mixture may actually qualify as an ink, slurry, or a paste. For example, the mixture may be applied as a solvent—or water-based slurry (50–1500 mPas) or as more of a paste (2500–12,000 mPas). The mixture may also be thermal sprayed as a dry powder mixture.

The mixture may be applied to at least a portion of the sensor element using at least one of printing, painting, caulking, rolling, spraying, pressure dispensing, thermal spraying and combinations thereof. The application method is chosen depending on the area to be covered and the layer thickness. The rheology of the slurry or paste is optimized accordingly for the chosen application process. The layer may be applied as a mono-, duplex-, or multi-layer directly or indirectly to the measuring electrode 31. In other words, the mixture may be applied directly to the measuring electrode, or may have one or more additional layers therebetween. For example, in one embodiment, the mixture may be applied to the electrode cover layer or porous protective layer 28, which covers the measuring electrode. This is shown, e.g., in FIGS. 3–6, wherein the coating 62, which is the result of the mixture being temperature treated, is applied (albeit indirectly) to the electrode 31. On the other hand, FIG. 7 shows the coating 62 being applied directly to the electrode 31 and substrate 21. Accordingly, as used herein, applying one substance to another, or one substance being "on" another substance, may mean directly or indirectly unless specifically stated otherwise.

In one embodiment, the mixture (i.e., ink, slurry, paste, powder etc.) may be applied in such a way that the mixture does not touch or cover the edges of a substrate or planar element to which it is applied. The substrate, e.g., may be the electrolyte foil 21, electrode 31, or protective layer 28, among others. By not covering the corners and edges of the planar substrate with the contamination-resistant coating 62 (the product of temperature treating the mixture), cracks which may usually originate and perpetuate themselves from stress points on the edges may be avoided. This results in a particularly robust design against damage by mechanical impact or thermal shock and allows for application of layers near the upper limit of the thickness range. FIG. 7 shows the coating 62 being applied in such a manner that the coating 62 does not cover the edges 64, 68 of the substrate 21. Any of the substrates to which the coating 62 adheres may have a plurality of edges, at least one of which the coating 62 may not cover. This leaves a part of the substrate that is not covered by the contamination-resistant coating 62, and to which an adhesive (discussed below) may adhere to further secure the coating.

In another embodiment, a thin adhesion layer may be used to further improve adhesion of the contamination-preventing layer to the measuring electrode. The adhesion layer may be applied directly to the electrode 31 or to the porous protective layer 28, which covers the measuring electrode 31. The thin adhesion layer may comprise at least one of a composition made from an oxide of boron, aluminum, magnesium, zirconium, silicon, and combinations thereof. The adhesion layer may be continuous, or it may be textured, i.e., it may be the product of windows or dots. Generally, the thickness of the adhesion layer is less than about 10 μm. More particularly, the thickness is generally less than about 8 μm, and even more particularly, less than about 5 μm. The thickness of the adhesion layer may be generally greater than about 0.1 μm, and is usually greater than about 0.5 μm or about 1 μm.

In a different application embodiment, the surface of a co-sintered electrode cover layer or protective layer 28 is mechanically structured to further improve adhesion of said contamination-preventing layer. Again, these layers may be made from A—or Zr-oxides. Typical mechanical structuring may include grinding, cutting, and combinations thereof. In yet a further embodiment, the surface of a electrode cover layer or porous protective layer 28 may be structured prior to co-sintering to further improve adhesion of said contamination-preventing layer. An example for this type of structuring is to screen print patterns such as lines, grids, or dots.

FIGS. 3–7 illustrate additional application embodiments. For these embodiments, a dense adhesive paste 54 having strong adhesive power may be applied using one of the ways shown in FIGS. 3–6, or a combination thereof, to connect the layer 28, substrate 21, or both with the washcoat 62 in a frame—or clamp-like fashion. Generally the paste has a very low porosity, and therefore, would render the sensor element as non functioning if it were applied on to the electrode or electrode protective layer. The adhesive or paste may comprise B, Si, or Na compounds. Examples of such a paste include, but are not limited to, Cercoat® and Bondceram® brands that may be obtained from Hottec Inc., Norwich, Conn. Applying the adhesive as shown in FIGS. 3–6 increases the mechanical robustness and stability of the washcoat. The robustness of these designs against protective layer damage by mechanical impact or thermal shock is superior.

Figure 3:
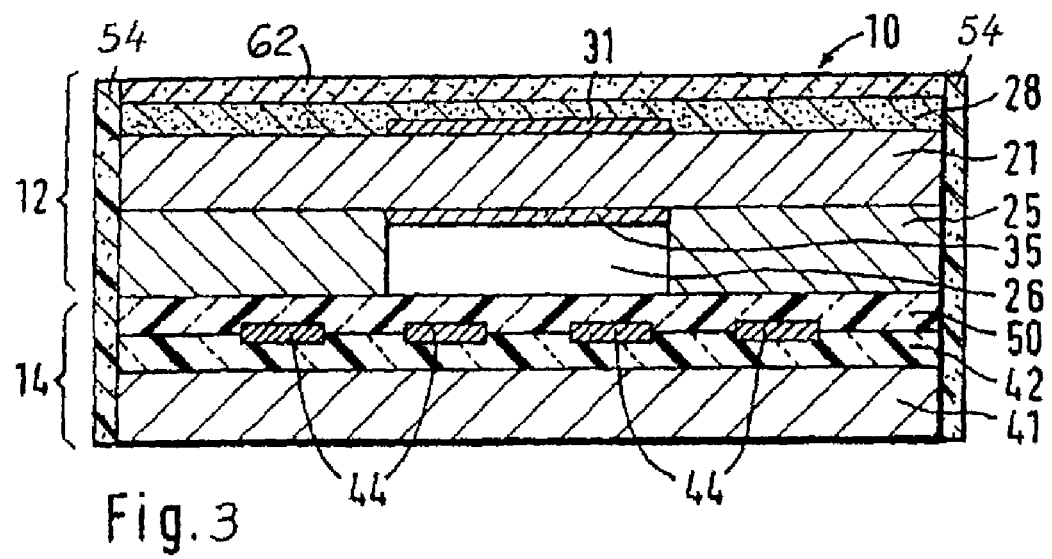
FIG. 3 shows a cross-section (similar to FIG. 1), in which a contamination-resistant coating is applied using an adhesive.

Again, FIGS. 3–7 are each cross-sections similar to the cross-section shown in FIG. 1. More particularly, FIG. 3 shows the adhesive paste 54 being applied to the sides of the layer 28, as well as the sides of the coating 62. In fact, the adhesive 54 may be applied to an entire side or sides of the sensor element 10 as shown in FIG. 3.

FIGS. 4–7 more clearly show the washcoat or protective coating 62 being applied in such a manner that it does not extend to the edges of the substrate 21 to which it is either directly or indirectly applied. The coating 62 may also not extend to at least one of the edges of the layer 28 to which it may be applied (not shown).

Figure 4:
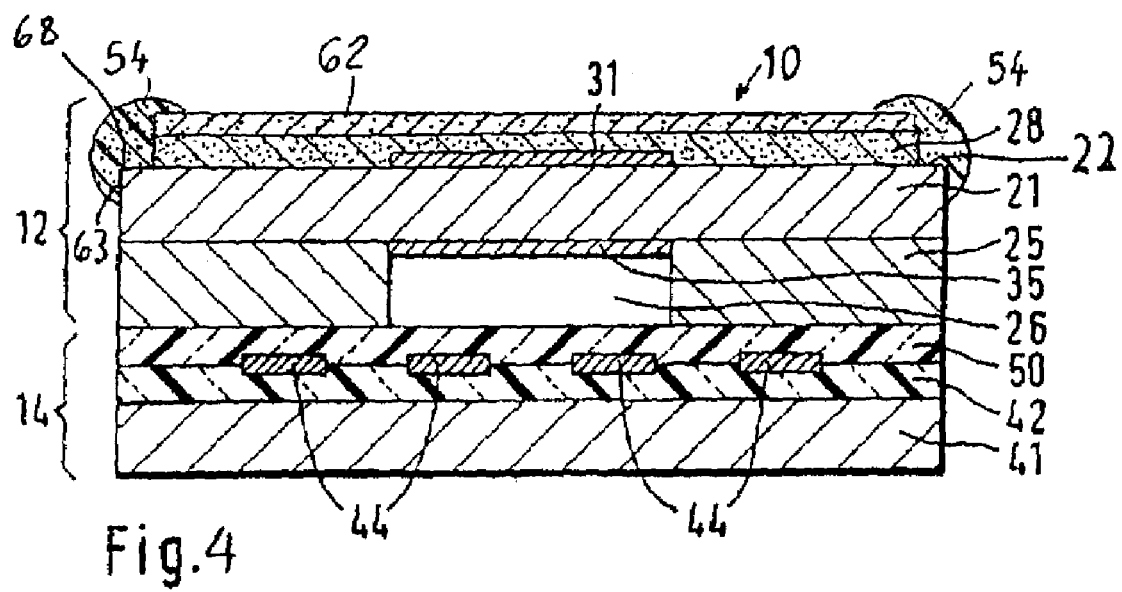
FIG. 4 shows a cross-section (similar to FIG. 1), in which another contamination-resistant coating is applied using a different adhesive application technique.

FIG. 4 shows the adhesive paste 54 being applied as a frame only on the upper edges of the substrate 21, as well as the outer edges of the layer 28 and protective coating 62. The adhesive 54 may also be applied to the top surface 22 of the substrate 21 as well as its side 63. The adhesive 54 may be applied to the top surface 22 of the substrate 21, such that it touches or covers one or both of the substrate's 21 edges 68. FIG. 4 shows the adhesive being applied to fill this gap between the coating 62 and the outer edge 68 of the substrate 21 as, again, the coating 62 may not extend to the substrate's edges for the reasons set forth above. In an alternative embodiment layer 28 may be eliminated.

Figure 5:
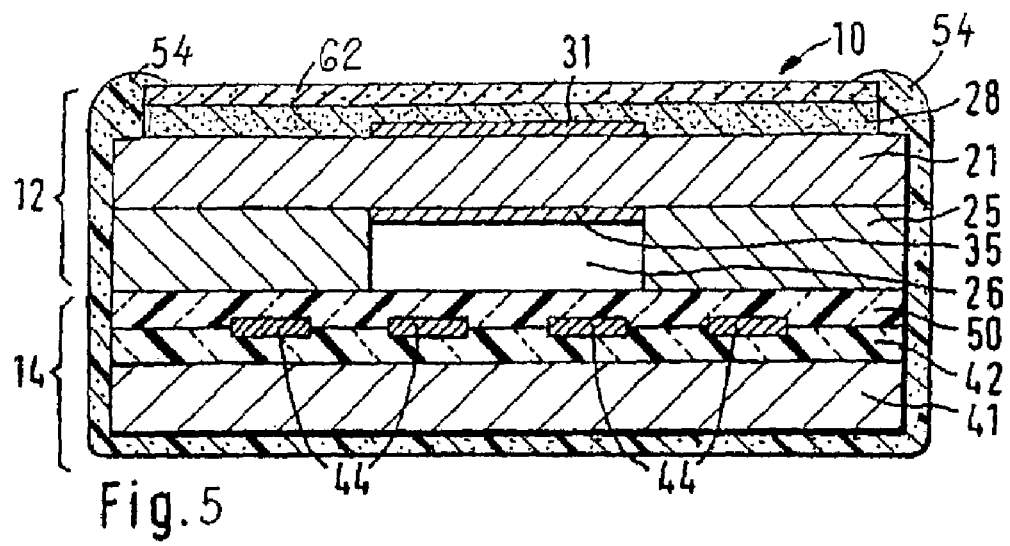
FIG. 5 shows a cross-section (similar to FIG. 1), in which another contamination-resistant coating is applied using a different adhesive application technique.

FIG. 5 shows another variation of the adhesive system set forth in FIG. 4. More particularly, the adhesive 54 starts from its position shown in FIG. 4, but extends around three sides of the sensor element. In an alternative embodiment, layer 28 may be eliminated.

Figure 6:
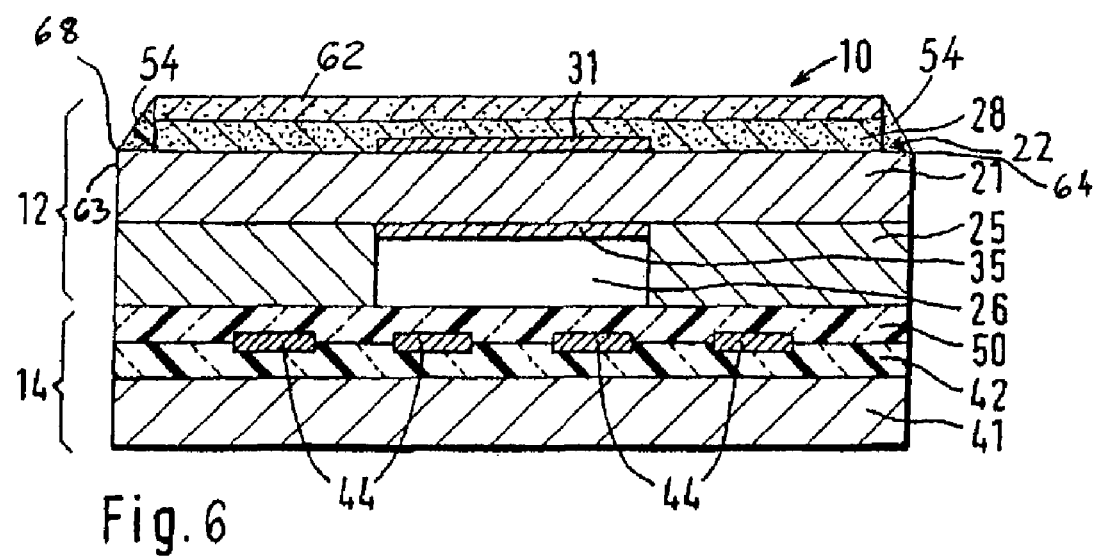
FIG. 6 shows a cross-section (similar to FIG. 1), in which another contamination-resistant coating is applied using a different adhesive application technique.
Figure 7:
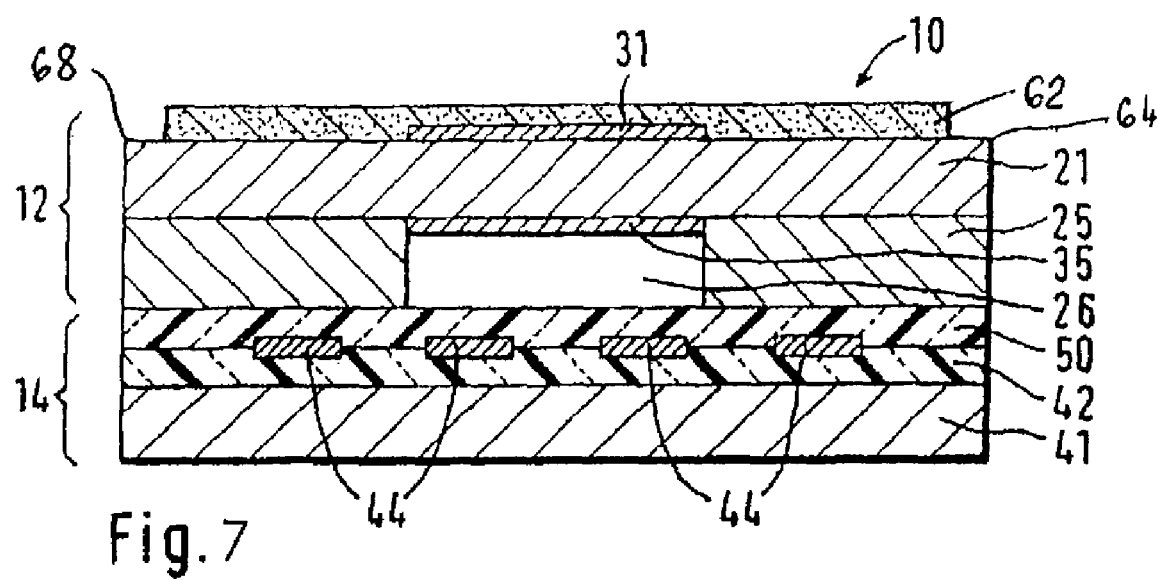
FIG. 7 shows a cross-section (similar to FIG. 1), in which no protective porous layer is applied to the sensor element, to which the contamination-resistant coating adheres.

FIG. 6 shows another adhesive variation. In this embodiment, the adhesive 54 only adheres to the top surface 22 of the foil or substrate 21, and not its sides 63. The adhesive 54 fills the gap between the coating 62, layer 28 and edges 64, 68 of the substrate 21. Again, layer 28 in this embodiment may be eliminated.

In summary, while FIGS. 3–6 show the coating 62 being applied to layer 28, which ultimately adheres to substrate 21, the layer 28 may be eliminated in any of the embodiments. FIG. 7 shows the coating 62 being applied directly to the substrate 21. Any of the adhesive techniques shown in FIGS. 3–6 may be applied to the embodiment shown in FIG. 7. Alternatively, at least one of layer 28 and coating 62 may extend to one or more edges of the substrate 21.

The contamination-resistant layer may have boundaries that are rounded. The rounded boundaries of the contamination-preventing layer may be controlled by the paste rheology (shear stability). In other words, the rheological agents discussed above may control the coatings' shear stability. The boundaries may be controlled by printing, brushing, painting, caulking, or rolling the paste onto to the planar element surface. More particularly, the boundaries of the contamination-preventing layer may be controlled by using a frame or template to cover the edges of the planar element prior to applying the contamination-preventing layer by spraying, pressure-dispensing, dipping, or dry-powder application processes. The frames or templates may be used to ensure that the protective coating does not extend to the substrate's (to which it adheres) edges when so desired. Again, frames or templates may be used in conjunction with thermal spraying a dry powder mixture onto the sensor element.

After a mixture is applied to the substrate in one or more of the ways set forth above, the coating is temperature treated. A typical temperature treatment profile has a drying phase and a burnout phase. The drying phase is conducted at a temperature greater than about 25° C. The temperature, however, is generally less than about 150° C. The treatment generally takes place for greater than about 5 minutes, and more particularly greater than about 10 minutes. The drying phase generally lasts for less than about 12 hours. The burnout phase may be conducted for greater than 10 minutes, but may be greater than 30 minutes. It usually lasts for less than about 10 hours, and more particularly, less than about 8 hours. Temperatures at the burnout phase may be greater than about 150° C., and more particularly, greater than about 250° C. Temperatures may be less than about 1300° C., and even less than about 1200° C. at the burnout stage.

The post-fire layer or coating 62 may have a thickness of at least about 50 μm, but more particularly will be greater than about 150 μm, and even more particularly, greater than about 200 μm. The thickness may be less than about 1 mm, but more particularly less about 800 μm and even less than 600 μm.

Although any combination of the above coatings or application techniques may be used, the following illustrate a few specific embodiments.

In one embodiment, a planar oxygen sensor having a single layer of one of the coatings described herein may be used. The layer may adhere to the element using a continuous or textured adhesion layer made from a compound comprising boron, aluminum, magnesium or zirconium as discussed above. The application method may comprise at least one of painting, brushing, rolling, printing, or caulking. A single applied layer may have a total thickness of about 50 to about 150 μm. In this embodiment, the boundaries of the coating are rounded and controlled by the paste rheology (shear stability).

In another embodiment, a planar oxygen sensor having a single layer of one of the coatings described herein may be used. The surface of the electrode cover layer may be structured prior to co-sintering (e.g. pattern printing) to further improve adhesion of the contamination-preventing layer. The application method may comprise at least one of dipping, spraying, pressure-dispensing and thermal spraying. The single layer may have a total thickness of about 50 to about 300 μm. In this embodiment, a frame or template with the desired coating dimensions controls the boundaries of the coating.

In a different embodiment, a planar oxygen sensor having a double layer of one or more of the coatings described herein may be used. The coating may adhere to the element using a continuous or textured adhesion layer made from a compound comprising boron, aluminum, magnesium or zirconium. The coating may also adhere to the element by using one or more of the applications shown in FIGS. 3–6, and described above. The coating may have a total thickness of about 100 to about 600 μm, and a porosity in the range of about 20 to about 70 percent.

In another embodiment, a planar oxygen sensor having a multi layer system comprising one or more of the coatings described herein may be used. The surface of the co-sintered electrode cover layer (e.g. made from aluminum or zirconium oxides) may be mechanically structured (e.g. by grinding) to further improve adhesion of the coating. The coating may also adhere to the element by using one or more of the applications shown in FIGS. 3–6, and described above. The coating may have a total thickness of about 200 to about 900 μm, and a porosity in the range of about 20 to about 70 percent.

In a different embodiment, a limit current sensor having a single layer of one or more of the coatings described herein may be used. The coating may adhere to the element using a continuous or textured adhesion layer made from a compound comprising boron, aluminum, magnesium or zirconium. The coating may also adhere to the element by using one or more of the applications shown in FIGS. 3–6, and described above. The coating may have a total thickness of about 50 to about 150 μm, and a porosity in the range of about 20 to about 70 percent.

In another embodiment, a limit current sensor having a double layer of one or more of the coatings described herein may be used. The coating may adhere to the element using a continuous or textured adhesion layer made from a compound comprising boron, aluminum, magnesium or zirconium. The coating may also adhere to the element by using one or more of the applications shown in FIGS. 3–6, and described above. The coating may have a total thickness of about 100 to about 300 µm, and a porosity in the range of about 20 to about 70 percent.

The Examples that follow are for illustrative purposes only, and in no way should be construed to limit the scope of the invention.

EXAMPLES

Example 1

Slurry with MgTiO₃

In one example, a low viscosity contamination-resistant washcoat slurry was prepared using the following: 70.0 g water; 1.5 g of a low-temperature organic binder, namely, Elvanol™ obtained from DuPont Corp.; 4.4 g of boehmite alumina ($Al_2O_3$) Dispal®; 2.1 g magnesium titanate ($MgTiO_3$) obtained from Ferro Corp; 21.5 g gamma alumina ($Al_2O_3$) SCFa™; and 2.0 grams of lithium carbonate from Sigma-Aldrich Corp. The water was placed in a beaker and 1.5 g low-temperature binder was added thereto. An electric stirrer was used to mix the mixture until all binder was mixed into the water. Subsequently, 4.4 g of the Dispal™ was slowly added to the mixture over the course of about 7 minutes, and then mixed for about 20 minutes. The magnesium titanate and lithium compound were then added, and subsequently mixed for about 10 minutes. In addition, 21.5 g of the SCFa™ was slowly added over the course of about 20–30 minutes, and then mixed until no lumps existed in the mixture. This was then mixed for about one hour before application. Continuous stirring was required to keep particles in suspension. When particles began to settle and the viscosity increased a very small amount of nitric acid was added to decrease viscosity. The mixture was then applied to at least a portion of a sensor element. The surface area (measured in $meters^2/grams$) of the magnesium titanate/high-temperature binder was about 2, whereas the surface area of the boehmite alumina was about 115, and the surface area of gamma-delta alumina was about 130 to 160. The mixture was applied using both dipping and brushing procedures. In different examples, 1 to 3 layers of the mixture were applied. After being temperature treated, the final layer thickness of these coatings ranged from 50 to 900 microns. The final layer porosity was about 35–40 percent.

Example 2

Paste with MgTiO₃

One particular mixture made according to a process similar to that set forth in Example 1, resulted in a high viscosity contamination-resistant washcoat slurry prepared using the following: 60.0 g water; 2.0 g of a low-temperature organic binder, namely, Elvanol® obtained from DuPont Corp.; 6.2 g of boehmite alumina ($Al_2O_3$) Dispal™; 2.8 g magnesium titanate ($MgTiO_3$) obtained from Ferro Corp; 28.7 g gamma alumina ($Al_2O_3$) SCFa™ and 2.3 grams of lithium carbonate from Sigma-Aldrich Corp. The mixture was applied using pressure dispensing. In different examples, 1 to 2 layers of the mixture were applied. After being temperature treated, the final layer of these coatings was about 100 to 600 microns. The final layer porosity was about 35–40 percent.

Example 3

Slurry with Glass Additive

In another example, a low viscosity contamination-resistant washcoat slurry was prepared using the following: 70.0 g water; 1.5 g of a low-temperature organic binder, namely, Elvanol® obtained from DuPont Corp.; 4.4 g of boehmite alumina ($Al_2O_3$) Dispal™; 2.1 g glass frit powder, namely C153M™ obtained from Asahi Glass Company; 21.5 g gamma alumina ($Al_2O_3$) SCFa™; and 2.0 grams of lithium nitrate from Sigma-Aldrich Corp. The water was placed in a beaker and 1.5 g low-temperature binder was added thereto. An electric stirrer was used to mix the mixture until all binder was mixed into the water. Subsequently, 4.4 g of the Dispal™ was slowly added to the mixture over the course of about 7 minutes, and then mixed for about 20 minutes. The glass frit powder and lithium compound were then added, and subsequently mixed for about 10 minutes. In addition, 21.5 g of the SCFa™ was slowly added over the course of about 20–30 minutes, and then mixed until no lumps existed in the mixture. Continuous stirring was required to keep particles in suspension. When particles began to settle and the viscosity increased, a very small amount of nitric acid was added to decrease viscosity. The mixture was then applied to at least a portion of a sensor element. The surface area (measured in $meters^2/grams$) of the glass frit powder/high-temperature binder was about 1.4, whereas the surface area of the boehmite alumina was about 115, and the surface area of gamma-delta alumina was about 130 to 160. The mixture was applied using both dipping and brushing procedures. In different examples, 1 to 3 layers of the mixture were applied. After being temperature treated, the final layer thickness of these coatings ranged from 50 to 900 microns. The final layer porosity was about 40–45 percent.

Example 4

Paste with Glass Additive

One particular mixture made according to a process similar to that set forth in Example 3, resulted in a high viscosity contamination-resistant washcoat slurry prepared using the following: 60.0 g water; 2.0 g of a low-temperature organic binder, namely, Elvanol® obtained from DuPont Corp.; 6.2 g of boehmite alumina ($Al_2O_3$) Dispal™; 2.8 g glass frit powder C153M™ obtained from Asahi Glass Company; 28.7 g gamma alumina ($Al_2O_3$) SCFa™; and 2.3 grams of lithium nitrate from Sigma-Aldrich Corp. The mixture was applied using pressure dispensing. In different examples, 1 to 2 layers of the mixture were applied. After being temperature treated, the final layer of these coatings was about 100 to 600 microns. The final layer porosity was about 40–45 percent.

Example 5

Sensors having coatings of the present invention at the thicknesses below were able to pass a variety of contamination engine run tests. More particularly, the coatings set forth in Examples 1, 2, 3 and 4 below were applied to Nernst-type planar oxygen sensors using painting, rolling, dipping, brushing, printing, pressure-dispensing and dry-powder application processes at thicknesses of 50 μm, 150 μm, 3001 μm, 450 μm and 600 μm and then tested for 50 hours, 100 hours, 150 hours, and 200+ hours of contamination engine runs. During these tests, the sensors were positioned in an exhaust pipe, and exposed to engine exhaust gas. Different engine sizes were used. At least about 1.5 mL of a silicon compound (i.e. a sensor poison) was added per gallon of gasoline. Different alkyl disiloxanes were used as silicon additives. The tests were conducted at different temperatures for different durations. The t r–l switch time value at 350 degrees Celsius was then tested, wherein t stands for time, r stands for rich exhaust gas, and l stands for lean exhaust gas. Rich exhaust gas comprises very little oxygen and a surplus of combustibles, whereas lean exhaust gas comprises excess oxygen gas.

To pass these tests, the parts had to have a t r–l value at 350 degrees Celsius of better than about 150 milliseconds. T r–l values are well-known in the art. In other words, after being exposed to exhaust gas (containing silicon compounds from the silicon additives in the gasoline) for the periods below, the sensor elements still showed a t r–l switch time of less than about 150 milliseconds. Each of the coatings set forth in Examples 1–4 (at the thicknesses below) passed the contamination engine run tests for the following durations.

| Thickness | Test Result |
|---|---|
| 50 μm layer thickness | Passed 50 h contamination engine run |
| 150 μm layer thickness | Passed 100 h contamination engine run |
| 300 μm layer thickness | Passed 150 h contamination engine run |
| 450 μm layer thickness | Passed 200 h contamination engine run |
| 600 μm layer thickness | Passed 200 + h contamination engine run |
| Conventional Art | Failed 50 h contamination engine run |

Sensor performance of limit current planar oxygen sensors having coatings of the present invention was also tested to a different specification. The limit current characteristics changed less than 10 percent before and after the contamination.

| Thickness | Test |
|---|---|
| 150 μm layer thickness | Passed 100 h contamination engine run |
| 300 μm layer thickness | Passed 200 + h contamination engine run |
| Conventional art | Failed 50 h contamination engine run |

The thickness and active material selection for the coating may dictate the coating's capacity for absorbing sensor contaminants such as phosphorus and silicon. As shown the coatings still tend to allow for very good permeability to ensure fast sensor response.

The sensor displays an unchanged functional characteristic (e.g. response time) after prolonged exposure to exhaust gas in contamination engine runs. This is in contrast to conventional art which shows deteriorating sensor performance due to sensor poisoning by compounds of Pb, P, Si, Mn, Zn or other elements present in combustion engine exhaust gas. The sensor contamination resilience is correlated with the thickness of the contamination-preventing layer.

Example 6

Any of the mixtures described herein and hereafter may be applied using the following technique. First, a dispense unit cartridge was filled with a specified washcoat formulation, and a cartridge was attached to the dispensing unit. The element/sensor was layed flat with a sensing surface facing up. One layer of the washcoat was then dispensed over the sensing side surface which also comprised a thin adhesion layer, and the element was allowed to dry for about 15 minutes. The element was heat treated in an oven at about 800° C. for about 45 minutes.

Example 7

Example 7 is another variation of poison-resistant washcoat application instructions for a lab sample preparation. The element/sensor was layed flat and, using a brushing technique with a template, a first layer of washcoat was applied on the sensing side comprising also an adhesive layer. The element was then allowed to air dry for about 30 minutes. This process was repeated until at least 2 layers were applied, and the elements were then allowed to air dry over night. The element was heat treated in an oven at about 1000° C. for about 45 minutes.

Example 8

Example 8 is another variation of poison-resistant washcoat application instructions for a lab sample preparation. The sensor element was dipped into a container of washcoat slurry using a template exposing only the desired sensor surface to the slurry. The element/sensor was laid flat and, allowed to air dry for about 5 minutes. This process was repeated for a second layer and the sensors were then allowed to air dry over night. The sensor was then heat treated in an oven at about between 750° C. for about 2 hours.

Example 9

Using any of the application techniques methods described in Examples 6, 7, and 8 the formulation set forth in Example 2 was applied onto the sensor element as a single layer. After drying at 60° C. for 10 minutes, a frame of adhesion paste was applied along the edges and corners to further improve adhesion strength. The element was then heat treated at about 1000° C. for about 45 minutes.

Example 10

Using any of the application techniques described in Example 6, 7, and 8, the formulation set forth in Example 1 was applied to a sensor element. A total of 3 layers were applied, and after drying at 60° C., a frame of adhesion paste was applied along the edges and corners to further improve adhesion. The element was heat treated at about 1000° C. for about 2 hours.

Example 11

Using the application methods set forth in Examples 6, 7, and 8, a washcoat comprising the formulation set forth in Example 1 was applied to a sensor element. Two layers of the washcoat were applied, the sensor element was dried at room temperature for about 30 minutes and heat treated at about 800° C. for about 1 hour.

Example 12

Using the application methods of Example 6, 7, and 8, a washcoat comprising the formulation or as set forth in Example 4 was applied onto a sensor element sensor element surface also comprising a thin structured adhesion layer. Three layers of the washcoat were applied to the element, and the sensor element was dried at 60° C. for about 10 minutes and subsequently heat treated at about 1000° C. for about 1 hour.

Example 13

Using one of the application techniques methods described in Examples 6, 7, and 8, the formulation set forth in Example 3 was applied onto the sensor element surface also comprising a thin continuous adhesion layer. Three washcoat layers were applied, and the element was dried at 60° C. for 10 minutes and heat-treated at about 1000° C. for about 15 minutes.

Example 14

Using a rolling application technique, a washcoat comprising the formulation set forth in Example 2 was applied to a sensor element. A template was used in order to only expose a portion of the sensor element surface to the paste. One layer was applied onto the sensor, an adhesion frame was added after drying at 60° C., and heat treatment followed at 800° C. for about 45 minutes.

Example 15

Using a printing application technique, a washcoat comprising the formulation set forth in Example 4 was applied to a sensor element. The printing application was used to apply 2 layers onto the sensor element. One layer of washcoat was printed, then allowed to dry for about 5 minutes at 60° C., then a second layer was printed. The element having the washcoat thereon was heat treated at about 1000° C. for about 60 minutes.

Example 16

In another example, a contamination-resistant protective layer was applied to a sensor element by a thermal spray process. 5 kg of gamma alumina ($Al_2O_3$) was mixed with 0.41 kg of $MgTiO_3$ and 0.38 kg of Li-oxide in a tumble mixer. This powder mixture was applied to the sensor element by plasma gun thermal spray process using a template exposing only a defined area of the element to the powder spray. The sensor element surface comprised a thin continuous adhesion layer. In different examples, 1 to 3 layers of the powder were applied. Heat treatment followed at 1000° C. for 1 hour. The resulting layer porosity was about 50 percent.

We claim:

1. A sensor element comprising a contamination-resistant coating on at least a portion thereof, the coating comprising gamma-delta alumina and magnesium titanate.

2. The element of claim 1, wherein the coating has a thickness of about 200 to about 500 microns.

3. The element of claim 1, wherein the coating has a porosity of about 30 to about 60 percent.

4. The element of claim 1, wherein the coating comprises about 85 to about 95% by weight gamma-delta alumina and about 5 to about 15% by weight magnesium titanate.

5. The element of claim 4, wherein the coating has a thickness of about 200 to about 500 microns.

6. The element of claim 5, wherein the coating has a porosity of about 30 to about 60 percent.

7. The element of claim 4, wherein the coating has a porosity of about 30 to about 60 percent.

8. The element of claim 1, wherein the portion of the sensor element is a substrate having a plurality of edges, and wherein the coating does not touch or cover at least one of the edges.

9. The element of claim 8, wherein the substrate is a surface of an electrolyte foil, and the surface has an exposed portion that is not covered by the coating.

10. The element of claim 9, wherein the coating at least partially covers an electrode.

11. The element of claim 1, wherein the portion of the sensor element is a protective layer comprising at least one of zirconium oxide, aluminum oxide, titanium oxide, magnesium oxide, and a combination thereof.

12. The element of claim 1, wherein the sensor element is a part of a stoichiometric or wide band automotive exhaust gas sensor.

13. A method of making a contamination-resistant sensor element:
   mixing gamma-delta alumina and magnesium titanate to form a mixture;
   applying the mixture to at least a portion of a sensor element; and
   temperature treating the mixture to form a contamination-resistant coating on the sensor element.

14. The method of claim 13, wherein the mixture further comprises boehmite alumina.

15. The method of claim 14, wherein the mixture comprises about 20 to about 25% by weight gamma-delta alumina, about 2 to about 4% by weight magnesium titanate, and about 2 to about 4% by weight boebmite alumina 16. The method of claim 14, wherein the mixture further comprises a low temperature binder.

17. The method of claim 16, wherein the low-temperature binder comprises at least one of hydroxyethyl cellulose, polyvinyl alcohol, polyvinyl pyrrolidone, polyvinyl acetate, polyacrylic resins, and a combination thereof.

18. The method of claim 17, wherein the low temperature binder comprises polyvinyl alcohol.

19. The method of claim 16, wherein the mixture comprises about 20 to about 25% by weight gamma-delta alumina, about 2 to about 4% by weight magnesium titanate, about 2 to about 4% by weight boebmite alumina, and about 0.5 to about 1.5 % by weight low temperature binder.

20. The method of claim 19, wherein the contamination-resistant coating comprises about 85% to about 95% by weight gamma-delta alumina and about 5% to about 15% by weight magnesium titanate and has a thickness of about 200 to about 500 microns and a porosity of about 30% to about 60%.

21. The method of claim 14, wherein the portion of the element is a substrate having a plurality of edges, and the coating does not touch or cover at least one of the edges.

22. The method of claim 21, wherein the substrate is a surface of an electrolyte foil, and the surface has an exposed portion that is not covered by the coating.

23. The method of claim 22, wherein an adhesive is used to secure the coating to the substrate, and the adhesive adheres to at least a portion of the exposed portion and at least a portion of the coating.

24. The method of claim 23, wherein the electrolyte foil has a side, and the adhesive adheres to at least a portion of the side.

25. The method of claim 24, further comprising a protective layer comprising at least one of zirconium oxide, aluminum oxide, titanium oxide, magnesium oxide, and a combination thereof, the protective layer being positioned between the coating and the foil.

26. The method of claim 14, wherein the portion of the sensor element is a protective layer.

27. The method of claim 26, wherein the protective layer is mechanically structured to improve adhesion between the coating and the sensor element.

28. The method of claim 27, wherein the protective layer comprises at least one of zirconium oxide, aluminum oxide, titanium oxide, magnesium oxide, and a combination thereof.

29. The method of claim 14, wherein the sensor element is a part of an automotive exhaust gas sensor.

30. The method of claim 29, wherein the automotive exhaust gas sensor is a stoichiometric or wide band sensor.

31. The method of claim 13, wherein the mixture is temperature-treated by drying the mixture at room temperature for at least about 15 minutes and then heating the mixture in the range of about 500 C. to about 1000° C. for about 45 minutes to about 8 hours.

32. A sensor element comprising:

a substrate having a plurality of edges;

a contamination-resistant coating comprising gamma-delta alumina and magnesium titanate applied to at least a portion of the substrate such that the coating does not touch or cover at least one of the edges, thereby leaving an exposed part of the substrate not covered by the coating; and an adhesive adhering to at least a portion of the exposed part and at least a portion of the coating to secure the coating to the substrate.

* * * * *

UNITED STATES PATENT AND TRADEMARK OFFICE
CERTIFICATE OF CORRECTION

PATENT NO. : 7,211,180 B2
APPLICATION NO. : 10/361872
DATED : May 1, 2007
INVENTOR(S) : Dr. Jens Stefan Schneider et al.

It is certified that error appears in the above-identified patent and that said Letters Patent is hereby corrected as shown below:

| | |
|---|---|
| Column 6, line 35 | Replace " A— " with --A1-- |
| Column 11, line 3 | Replace "3001" with --300-- |
| Claim 19, line 4 | Replace "boebmite" with --boehmite-- |
| Claim 31, line 4 | Replace "500 C." with --500°C.-- |

Signed and Sealed this

Seventeenth Day of July, 2007

JON W. DUDAS
*Director of the United States Patent and Trademark Office*